United States Patent [19]

Nguyen

[11] Patent Number: 5,096,585
[45] Date of Patent: Mar. 17, 1992

[54] PROCESS FOR PREPARING PROTEIN NON-ADSORPTIVE MICROPOROUS POLYSULFONE MEMBRANES

[75] Inventor: Thanh D. Nguyen, Billerica, Mass.

[73] Assignee: W. R. Grace & Co.-Conn., New York, N.Y.

[21] Appl. No.: 646,977

[22] Filed: Jan. 28, 1991

[51] Int. Cl.$^5$ .................. B01D 63/04; B01D 69/08
[52] U.S. Cl. .................. 210/500.23; 210/500.41; 264/177.15
[58] Field of Search .................. 264/41, 174, DIG. 48, 264/556, DIG. 62, 45, 1, 298, 177.15, 177.14, 178 F, 212–215, 500.41, 500.23

[56] References Cited

U.S. PATENT DOCUMENTS

| | | |
|---|---|---|
| 3,691,068 | 9/1972 | Cross . |
| 4,029,582 | 6/1977 | Ishii et al. . |
| 4,207,182 | 6/1980 | Marze . |
| 4,320,463 | 10/1980 | Henis et al. .................. 264/41 |
| 4,612,119 | 9/1986 | Eguchi . |
| 4,744,932 | 5/1988 | Browne . |
| 4,772,391 | 9/1988 | Baker et al. . |
| 4,970,034 | 11/1990 | Ly et al. .................. 264/41 |

FOREIGN PATENT DOCUMENTS

| | | |
|---|---|---|
| 100285 | 9/1986 | European Pat. Off. . |
| 172312 | 9/1985 | Japan . |
| 1000410 | 1/1986 | Japan . |
| 1028409 | 2/1986 | Japan . |
| 1057628 | 3/1986 | Japan . |
| 1113460 | 5/1986 | Japan . |
| 2388834 | 10/1986 | Japan . |
| 2174641 | 11/1986 | United Kingdom . |

OTHER PUBLICATIONS

Cabasso et al., J. Appl. Pol. Sci., vol. 20, pp. 2377–2394, 1976.
Cabasso et al., J. Appl. Pol. Sci., vol. 21, pp. 165–180, 1883–1900, 1977.
Aptel et al., J. Mem. Sci., vol. 22, pp. 199–215, 1985.
Nguyen et al., North American Membrane Society, presented May 17, 1989.

*Primary Examiner*—Frank Sever
*Attorney, Agent, or Firm*—Vanessa L. Appleby; Jill H. Krafte; Steven T. Trinker

[57] ABSTRACT

Microporous polysulfone membranes can be prepared by using a particular combination of casting solution and precipitation solution formulations, and casting conditions. The casting solution comprises polysulfone and a protein non-adsorptive prepolymer and the precipitation solution comprises a polymerization catalyst. Both hollow fiber and flat membranes can be prepared in this manner. The membranes are substantially protein non-adsorptive and have valuable physical characteristics including increased strength and high flux.

17 Claims, 1 Drawing Sheet

PROCESS FOR PREPARING PROTEIN NON-ADSORPTIVE MICROPOROUS POLYSULFONE MEMBRANES

TECHNICAL FIELD

This invention relates to the preparation of microporous polysulfone membranes. More specifically, the membranes prepared according to this invention have high burst strength, high flux and low protein adsorption characteristics suitable for applications to biotechnology. These characteristics are achieved by using a novel combination of casting solution, precipitation solution and spinning conditions. More particularly, the casting solution contains a polymerization hydrophilic protein non-adsorptive prepolymer and the precipitation solution contains a polymerization catalyst. The presence of the catalyst facilitates the polymerization of the prepolymer at the membrane/precipitation solution interface forming an inter-penetrating polymer network. Liquid-liquid membrane precipitation or coagulation is employed.

BACKGROUND OF THE INVENTION

Polysulfone membranes and hollow fiber membranes are known to the art and have been prepared to a variety of specifications. However, prior art hollow fibers typically are asymmetrical, or anisotropic. This type of fiber comprises a "skin" at the inner and/or outer surface and a microporous understructure. For example, U.S. Pat. No. 3,691,068 (Cross) discloses an anisotropic microporous polysulfone polymer membrane having a barrier layer at a surface thereof and a more porous support layer integral with the barrier layer. Similarly, U.S. Pat. No. 4,029,582 (Ishii et al.) discloses poly(arylethersulfone) semipermeable membranes having a thin dense layer and a porous supporting layer.

Skinless polysulfone hollow fibers are known to the art. U.S. Pat. No. 4,612,119 (Eguchi) discloses preparation of a polysulfone hollow fiber filter medium having substantially no skin layer at the outer and inner surface areas. Eguchi uses a dry-wet spinning process, with carefully controlled temperatures. Cabasso et al., "Polysulfone Hollow Fibers II. Morphology," J. Applied Polymer Science, Vol. 21, pp. 165–80 (1977), which also utilizes a dry-wet spinning method, reports that control of the extrusion/coagulation procedure allows the formulation of skinned, porous skinned and non-skinned fibers. In a dry-wet spinning process, the membrane casting solution is extruded into an air space and then is conducted into a liquid precipitation medium.

A major drawback of using membranes for concentration or fractionation of proteins in biotechnology downstream separation processes is the adsorption of protein molecule solutes on the membrane surface. This has an important impact on the flux decline, usually called "membrane fouling," and the performance characteristics of the membrane change with operating time. As a consequence, the separation process design becomes more difficult to optimize and sometimes requires complex operation modes. The easiest way to overcome this problem is to employ a protein non-adsorptive membrane.

U.S. Pat. No. 4,787,976 (Parham) discloses protein non-absorptive filtration membranes which does not include a catalyst in the coagulation solution. U.S. Pat. No. 4,970,034 (Ly) discloses a process for preparing microporous polysulfone membranes. Since there is no catalyst in the Ly coagulation solutions, the membranes formed do not have the increased strength, flux and protein non-adsorptive characteristics of the present invention.

SUMMARY OF THE INVENTION

The process of this invention allows for the preparation of substantially protein non-absorptive polysulfone microporous membranes. The membranes are nearly homogeneous from surface to surface.

It is a primary object of this invention to provide substantially protein non-adsorptive polysulfone microporous membranes. In relation to this, it is desired that the membranes have a hydrophilic characteristic membrane surface together with a strong membrane wall structure. As a result, the membranes exhibit high burst strength, excellent fluxes, low fouling properties, as well as easy cleaning for re-use due to very low protein adsorption on the membrane surface.

It is intended that this process provide protein non-adsorptive membranes which display high fluxes by addition of a hydrophilic, low reactive prepolymer having substantially protein non-adsorptive properties into the membrane casting solution. The membrane is precipitated in a coagulating solution in the presence of a polymerization catalyst. The catalyst is used to accelerate the polymerization of the prepolymer.

It is intended that this process offer the ability to control the porosity and membrane wall thickness. At the same time, however, it is expected that membranes prepared in this manner will have more flexibility with respect to application and quality control than would be true of the prior art anisotropic membranes, by virtue of the uniformity of the membrane wall structure. For these membranes of this invention, the entire wall, rather than just the skin portion, performs the filtration. For that reason, it is expected that minor imperfections in isolated portions of the wall will not affect or impair the ability of the membrane to function.

It is another object to teach appropriate spinning and setting conditions to allow for the formation of hollow fiber membranes.

Still another object is to provide membranes which are useful in industrial or pharmaceutical protein fractionation. As one specific purpose, it is intended to provide membranes which are substantially protein non-adsorptive, exhibit high rejection of high molecular weight materials, while allowing lower molecular weight materials to flow through. As another specific purpose, it is intended to provide membranes with a high surface area of polymer in the membrane wall in order to afford a high concentration of immobilization sites for cells or other bioactive agents.

DETAILED DESCRIPTION OF THE INVENTION

Figure 1:
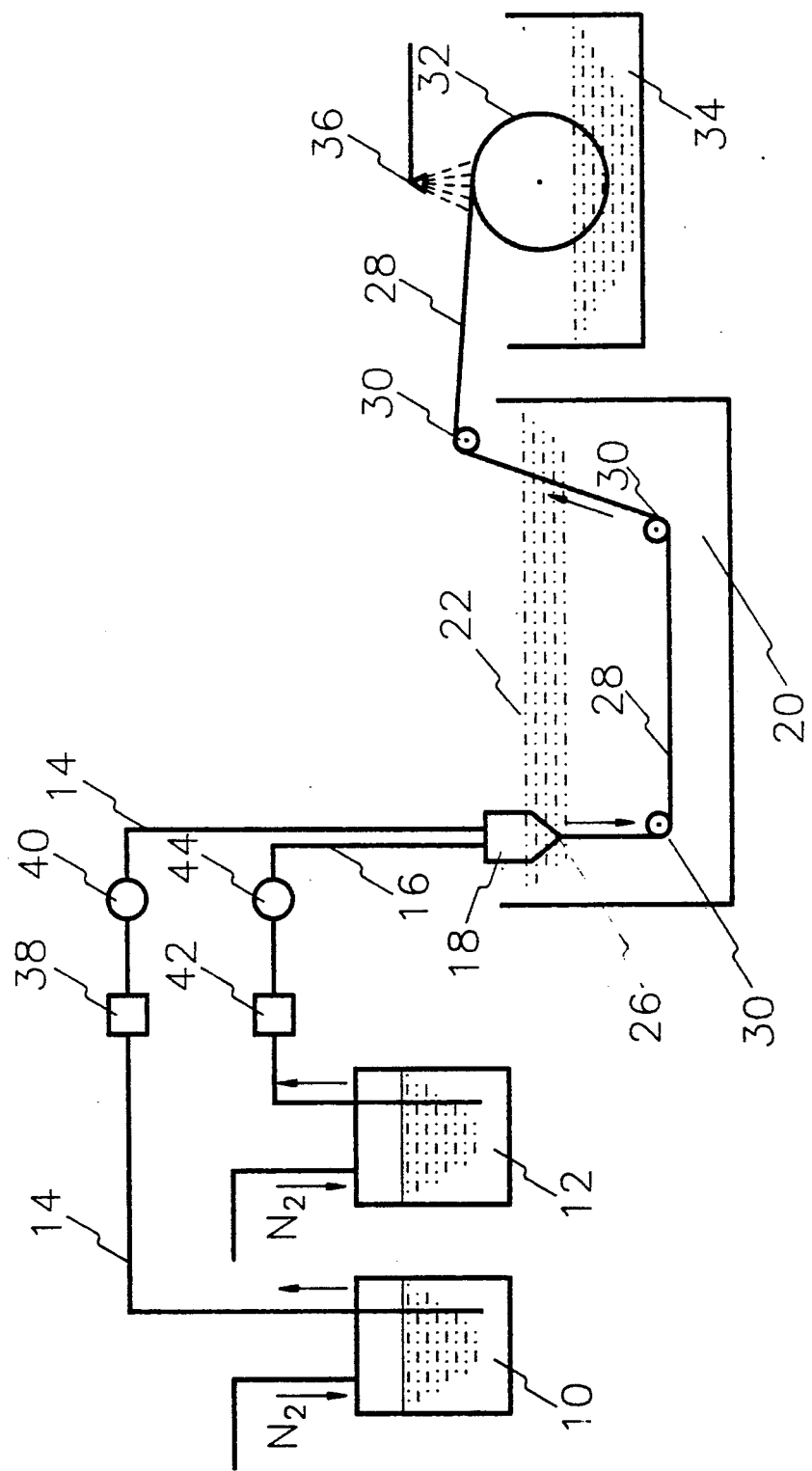
FIG. 1 is a schematic diagram of the hollow fiber membrane spinning process embodiment used in Examples I and II.

A method of membrane preparation has been discovered by which substantially protein non-adsorptive polysulfone membranes may be prepared in hollow fiber or flat sheet form. One way of enabling the finished membrane to be protein non-fouling is to use a protein non-adsorptive prepolymer as the prepolymer in the membrane casting solution. A membrane surface which does not adsorb protein will not be subject to the fouling problem since the proteinaceous layer does not adhere to the surface.

The porous membranes of this invention are manufactured by a phase inversion process in a liquid-liquid precipitation scheme. This process involves the conversion of a liquid homogeneous polymer solution (casting solution) comprising a polysulfone polymer and a hydrophilic substantially protein non-adsorptive prepolymer into a solid, but flexible, porous fiber. The casting solution contains two or more polymers, one or more solvents for the polymer(s) and one or more nonsolvents for the polymer(s). The non-solvent acts as a pore-former and hereafter the non-solvent used in the casting solution will be referred to as a pore-former or pore-forming agent or compound.

The casting solution is extruded directly into a liquid precipitation medium, where formation of the membrane occurs by phase inversion, that is, by precipitation of the polymeric component from the casting solution. This is referred to as liquid-liquid phase separation. In the case of hollow fiber formation, it may also be known as wet spinning. In that embodiment, the casting solution is fed through an extrusion die (spinnerette) directly into an outer precipitation solution, while simultaneously introducing a center precipitation solution through the central aperture of the spinnerette to mechanically maintain the hollow center hole of the fiber where formation of a flat sheet membrane is desired, the casting solution is cast directly into a precipitation solution, onto a flat support.

During the initial contact with the precipitation solutions, solvent and pore former are drawn from the casting solution. As a result, the polymer concentration increases and then causes precipitation of the polymer from the casting solution. The membrane continues to form as both solvent and pore-former are leached out and the polymer precipitates completely. The precipitation solution contains a polymerization catalyst which is used to accelerate the polymerization of the prepolymer. During the membrane formation process, prepolymer leaches almost completely out of the membrane together with the pore-forming agent and the solvent into the coagulating solution. When the prepolymer reaches the membrane surface, a small amount of prepolymer is polymerized upon contact with the catalyst at the membrane/coagulating solution interface; an interpenetrating polymer network is formed, and it is retained on the membrane surface. As a result, the membrane obtained has a strong wall structure coupled with hydrophilic, protein non-adsorptive surface.

The factors influencing membrane porosity, pore size, membrane strength and overall morphology are exceedingly complex. It has been discovered that a particular combination of these factors, i.e., casting solution, precipitation solution and spinning conditions, particularly the inclusion of substantially protein non-adsorptive prepolymers and catalysts, will yield a strong, protein non-adsorptive polysulfone microporous hollow fiber membrane.

Casting Solution

As described above, the casting solution is a multi-component solution comprising polymeric, solvent and non-solvent (pore-forming) components. The primary polymeric components will be a polysulfone polymer and a substantially protein non-adsorptive prepolymer. The polymeric component would, of course, also comprise any other polymer(s) or prepolymer(s) used together with the PS polymer and prepolymer to form the membranes. Where reference is made to the polysulfone solution or casting solution, it is intended to include all polymeric components. That is, it will include the polysulfone polymer, the protein non-adsorptive prepolymer, and, where appropriate, it also will include a selected additional polymer or prepolymer.

A. Polymeric Components a. Polysulfone

The membranes of this invention are polysulfone-based polymeric compositions. Polysulfone (PS) polymers are available in a variety of grades with respect to molecular weight, additives, etc. High molecular weight polysulfones may be preferred for preparation of membranes with additional strength Udel TM 3500 and Udel TM 1700 polysulfone polymers (Amoco Performance Products Inc.) are suitable. Polysulfone is used as the primary polymeric component of the membrane because of such beneficial characteristics as thermal stability, resistance to acid, alkali and salt solutions, high mechanical strength, etc.

b. Protein Non-Adsorptive Prepolymers

The substantially protein non-adsorptive prepolymers used in this invention are hydrophilic isocyanate end-capped polyurethane prepolymers. The preferred prepolymer is a polyol made up of at least 75% oxyethylene monomers. The polyols have molecular weights of about 7000 to about 30,000, with essentially all of the hydroxyl groups capped with polyisocyanate. The prepolymers are prepared by reacting selected polyols with polyisocyanate at an isocyanate-to-hydroxyl ratio of about 1.8 to about 2.2 so that essentially all of the hydroxyl groups of the polyols are capped with polyisocyanate. As specific examples of this class of prepolymers, prepolymers from the BIOPOL TM polyurethane prepolymer series available from Grace Specialty Chemicals Co., W. R. Grace & Co.-Conn., will be particularly suitable.

High molecular weight ethylene oxide-based polyols are preferably used to prepare the prepolymers of the present invention. The polyol molecular weight prior to capping with polyisocyanate should be about 7000 to about 30,000 MW. It is preferred to use trihydroxy compounds (triols) in the preparation of the polyols which are the precursors to the prepolymers and hydrated polymers of this invention. For example, glycerol is a preferred triol. Trimethylolpropane (TMOP), trimethylolethane and triethanolamine are other suitable triols. In addition, tetrols, such as pentaerythritol, may be used to prepare polyols for use in this invention. Triol- or tetrol-based polyols are capped with difunctional or polyfunctional isocyanate compounds as described below to form the prepolymer.

The prepolymers of this invention are formed by reacting the hydroxyl groups of the olyols described above with polyisocyanates. "Polyisocyanate" as used herein is intended to refer to both diisocyanates and polyisocyanates, as appropriate, except as indicated by specifying the use of difunctional or polyfunctional isocyanates. Isocyanate end-capped (i.e., isocyanate-terminated) prepolymers are formed. The choice of the polyisocyanate will depend on such factors as biocompatibility of the end product and differential NCO reactivities.

Aliphatic and cycloaliphatic polyisocyanates are preferred for use in this invention, although aromatic polyisocyanates may occasionally be used. Aliphatic polyisocyanates are the most preferred because of decreased toxicological considerations.

Examples of suitable di- and polyfunctional isocyanates are found in the following list.
toluene-2,4-diisocyanate
toluene-2,6-diisocyanate
commercial mixtures of toluene-2,4 and 2,6-diisocyanates
isophorone diisocyanate
ethylene diisocyanate
ethylidene diisocyanate
propylene-1,2-diisocyanate
cyclohexylene-1,2-diisocyanate
cyclohexylene-1,4-diisocyanate
m-phenylene diisocyanate
3,3'-diphenyl-4,4'-biphenylene diisocyanate
4,4'-biphenylene diisocyanate
4,4'-diphenylmethane diisocyanate
3,3'-dichloro-4,4'-biphenylene diisocyanate
1,6-hexamethylene diisocyanate
4-tetramethylene diisocyanate
1,10-decamethylene diisocyanate
cumene-2,4-diisocyanate
1,5-napthalene diisocyanate
methylene dicyclohexyl diisocyanate
1,4-cyclohexylene diisocyanate
p-tetramethyl xylylene diisocyanate
p-phenylene diisocyanate
4-methoxy-1,3-phenylene diisocyanate
4-chloro-1,3-phenylene diisocyanate
4-bromo-1,3-phenylene diisocyanate
4-ethoxy-1,3-phenylene diisocyanate
2,4-dimethyl-phenylene diisocyanate
5,6-dimethyl-1,3-phenylene diisocyanate
2,4-diisocyanatodiphenylether
4,4'-diisocyanatodiphenylether
benzidine diisocyanate
4,6-dimethyl-1,3-phenylene diisocyanate
9,10-anthracene diisocyanate
4,4'-diisocyanatodibenzyl
3,3'-dimethyl-4,4'-diisocyanatodiphenyl methane
2,6-dimethyl-4,4'-diisocyanatodiphenyl
2,4-diisocyanatostilbene
3,3-dimethoxy-4,4'-diisocyanatodiphenyl
1,4-anthracenediisocyanate
2,5-fluorenediisocyanate
1,8-naphthalene diisocyanate
2,6-diisocyanatobenzfuran
2,4,6-toluene triisocyanate
p,p',p"-triphenylmethane triisocyanate
trifunctional trimer (isocyanurate) of isophorone diisocyanate
trifunctional biuret of hexamethylene diisocyanate
trifunctional trimer (isocyanurate) of hexamethylene diisocyanate
polymeric 4,4'-diphenylmethane diisocyanate Capping of the selected polyols with polyisocyanates to form the prepolymers used in this invention is effected using stoichiometric amounts of reactants. The isocyanate-to-hydroxyl group ratio preferably should be between about 1.8 and about 2.2. Higher ratios may be used but are not preferred since they may lead to problems associated with excessive monomer present in the final products. The capping reaction may be by any convenient method or procedure. For example, the reaction may be carried out at about 20° to about 150° C., under dry nitrogen, for about 2 hours to about 14 days, preferably in the absence of a catalyst. The preferred temperature is about 125° C. The reaction is terminated when the isocyanate concentration approaches theoretical values. The time period will be a function of the polyol and the polyisocyanate used and the temperature at which the reaction is conducted. Polymerization occurs much more rapidly when aromatic polyisocyanates are used than with aliphatic polyisocyanates. Similarly, the reaction will be more rapid with increased temperatures.

It is preferred to avoid using an excess of polyisocyanate in preparing the prepolymer. Preferably, an isocyanate-to-hydroxyl group ratio of 2:1 (for example, one diisocyanate molecule per hydroxyl group of the polyol) is used to ensure complete end-capping of the polyol. Complete end-capping eliminates excessively high viscosity in the prepolymer by avoiding undue amounts of chain extension. However, a slight excess of isocyanate, i.e., up to about ten percent can be used.

It is characteristic of the present polymer system that the isocyanate content is very low. This is achieved by employing high molecular weight polyols and by avoiding excessive quantities of isocyanate in the end-capping reaction so that free isocyanate monomers are kept at a minimum. The isocyanate concentration in the prepolymer should be above 0.05 milliequivalents per gram and preferably about 0.1 to about 0.43 milliequivalents per gram, for prepolymers formed from triols or high polyols of about 7000 to 30,000 MW.

c. Other Polymers

Polysulfone alone is very hydrophobic. Addition of the isocyanate-capped polyurethane prepolymers results in membranes with increased resistance to nonspecific protein adsorption as well as enhanced biocompatibility. Whereas the polysulfone polymer precipitates out of the casting solution, a polyurethane prepolymer actually polymerizes upon contact with the aqueous precipitation solution.

Other polymers or prepolymers can be used in combination with the polysulfone polymer and protein non-adsorptive prepolymer, if desired, to impart various characteristics to the membrane product. Polyethylene glycol (PEG) or polyvinyl pyrrolidone (PVP) may additionally be used to prepare these membranes. Polymers or prepolymers such as these are added in order to modify the structure and surface characteristics of the membrane. The additional polymer or prepolymer becomes an integral part of the membrane structure.

B. The Solvent

The solvent component of the casting solution must be one in which polysulfone (as well as any other polymer or prepolymer used) is soluble. The polysulfone polymer is soluble in various solvents, such as N-methylpyrrolidone (NMP), dimethylformamide (DMF), N,N-dimethylacetamide (DMA), cyclohexanone, chloroform, and 4-butyrolactone. NMP is the preferred solvent.

At least about 8.0 wt. % and up to about 35.0 wt. % polysulfone in solvent should be used, preferably about 9.0 to about 18.0 wt. %. Above 35 wt. %, it will be difficult or impossible to dissolve the polysulfone in the solvent. Below about 8 wt. %, the precipitation rate will be too slow for formation of hollow fibers. The substantially protein non-adsorptive prepolymer should be present in the casting solution in an amount of about 1 wt. % to about 20 wt. %. Up to about 20.0 wt. % of a third polymeric component, that is, one or more of the polymers or prepolymers described above, can be added to the PS solution.

C. The Pore-Forming Component

Selection of the pore-forming component is very important for the ultimate characteristics of the membrane. Pore formation will vary depending on the interaction between the non-solvent (pore-former) and the other components of the casting solution, as well as the solubility of the pore-former in the precipitation solution, etc. The selection of the pore-forming agent will affect casting solution viscosity and rate of casting solution precipitation, as well as membrane porosity, permeability and morphology. The pore-forming component must be soluble in the precipitation solution used in the membrane formation process.

The polymer or prepolymer component which may be added in conjunction with the polysulfone could be considered a non-solvent in that it will not dissolve PS. However, although this component may partially leach out of the membrane, it does not completely leach out as do the precipitation medium-soluble non-solvents (pore-formers) listed below.

Generally, the pore-forming component can be selected from alkanols, polyols, polyglycols, cyclokotones or combinations thereof. Specific, but nonlimiting, examples include methanol, t-butanol, acetone, cyclododecanone, 4-hydroxybutyric acid and polyethylene glycol (PEG). The quantity used will vary and can be determined for each pore-forming composition by routine optimization. For low molecular weight pore-formers, it will be preferred to use larger quantities in the casting solution. Where high molecular weight pore-formers are used, such as high molecular weight PEG, they may not completely leach out of the membrane during normal processing.

Precipitation Solution

The precipitation or coagulation mechanism of membrane formation is affected by the composition of the precipitation solution as well as that of the casting solution, and the compositions of these two solutions are interdependent. In this disclosure, the terms "precipitation solution," "coagulation solution," "quench solution" and "quench bath" are used interchangeably to refer to the solution in which the membrane is formed. For formation of hollow fiber membranes, both an outer and a center precipitation or quench solution will be employed. The precipitation solution is made up of three essential components: solvent, non-solvent and swelling agent. Additionally, the center precipitation solution, and possibly the outer precipitation solution, contains a catalyst. Together, these components control the rate of membrane precipitation as well as the membrane characteristics, resulting in formation of the membrane of this invention.

A. The Solvent

The solvent content of the precipitation solution controls the rate at which the solvent comes out of the casting solution. In turn, this controls the rate of increase of the polymer concentration to the point at which the polymeric component precipitates out of the casting solution to form the membrane. The same solvent usually is used in the casting solution and the precipitation solution. NMP is the preferred solvent. Other solvents are discussed above with regard to casting solutions.

B. The Non-Solvent

A non-solvent is used in the precipitation solution in order to precipitate the polymer and prepolymer from the casting solution, thus causing formation of the membrane. For practical and economical purposes, it is preferred to use water as the non-solvent component of the precipitation solution. However, other non-solvents such as methanol, ethanol, propanol, butanol, ethylene glycol, acetone, methyl ethyl ketone, or the like, as listed above, can be used in conjunction with water, particularly when the solvent is water-immiscible.

C. The Swelling Agent

The presence of a swelling agent in the precipitation solution also serves to control the polymer and prepolymer precipitation rates. This component swells, but does not dissolve the polymer or prepolymer, thus slowing the rate of polymer precipitation. In addition, the presence of the swelling agent acts to favor the introduction of the precipitation medium into the casting solution, in exchange for the pore-former and solvent, resulting in the formation of a membrane with a high porosity. The preferred swelling agent is ethanol or isopropyl alcohol (IPA). Alternatively, other components, or combinations thereof, can be used as the swelling agent. Triethylene glycol, nitrobenzene, tetrahydrofuran, dioxane, dimethyl carbonate, dimethyl sulfone, diethyl phosphate and dimethyl sulfoxide may be used as swelling agents.

D. The Catalyst

The presence of a catalyst in the precipitation solution serves to accelerate the polymerization of the prepolymer. Most of the prepolymer leaches out of the membrane with the pore-former and solvent. However, when the polymerization catalyst is present in the coagulation solution, a small amount of prepolymer is polymerized upon contact with the catalyst at the interface between the membrane and coagulating solution. During this process, an interpenetrating network between the polysulfone and the polymerized prepolymer is formed. The membrane has a characteristic strong wall structure and hydrophilic, protein non-adsorptive surface which combination was previously unknown. Numerous catalysts known in the art can be used for this application. The preferred catalysts are water-soluble salts consisting of a monovalent cation of the alkali metal family or a divalent cation of the alkaline-earth metal family and an anion. Monovalent cations can be lithium, sodium, potassium, and cesium. Divalent cations can be calcium, strontium, barium, and magnesium. The anion can be carbonate, bicarbonate, borate, phosphate, nitrate, silicate, aluminate, and hydroxide. The most preferred catalysts include sodium bicarbonate, sodium nitrate, and sodium borate. Catalyst mixtures can also be used.

In the preferred embodiment of this invention, the precipitation solution is made up of N-methylpyrrolidone (NMP) as the solvent, ethanol or isopropanol as the swelling agent, water as the non-solvent, and sodium bicarbonate as the catalyst. About 10 to 70 wt. % NMP is used, preferably about 40 to 70 wt. %, most preferably about 50 to 70 wt. %. About 10 to 80 wt. % ethanol or isopropanol is used, preferably about 15 to 40 wt. %. About 5 to 40 wt. % water is used, preferably about 10 to 30 wt. %. About 0.01 to 1.0 wt. % sodium bicarbonate is used, preferably about 0.05 to 0.2 wt. %. Where other solvents, swelling agents, or catalysts are substituted for these preferred components, these general ranges will still be applicable.

Hollow Fiber Spinning Conditions

In preparing hollow fiber membranes of this invention, a liquid-liquid or wet spinning process is used. That is, the casting solution is fed through an extrusion die (spinnerette) directly into a precipitation bath, while simultaneously introducing the center quench fluid through the central aperture of the spinnerette to mechanically maintain the hollow center hole of the fiber. The fiber is fabricated and simultaneously quenched as it is drawn through the precipitation bath. By using this wet-spinning process, fibers with homogeneous pore structure and membrane morphology are produced.

One of the key factors in preparation of the hollow fiber membranes of this invention is use of the wet spinning process, that is, spinning the casting solution directly into the precipitation solution or bath. Wet spinning is also necessary since the catalyst is in the precipitation solution. It is important that the casting solution interact with the precipitation solution containing the catalyst in order to form the strong wall which is characteristic of this invention.

In addition, selection of appropriate solutions for the inner and outer precipitation baths is important, as is the appropriate drawing or spinning rate of the fiber as it is formed. The presence of the center quench fluid also allows for simultaneous polymer precipitation from both the inner and outer surfaces of the fiber. The spinning rate is adjusted to allow for exchange of components between the casting and precipitation solutions. The solvent and pore-forming agent are leached out of the casting solution and are replaced by the non-solvent and swelling agent from the precipitation solution. As a consequence, polymer precipitation occurs, leading to formation of the membrane.

Too rapid a drawing rate will cause breakage due to insufficient membrane formation to maintain membrane integrity or will cause elongation or deformation of the pores. Conversely, too slow a drawing rate will not be cost effective. The preferred drawing rate will depend in part on the casting solution viscosity and temperature and in part on the factors described below. However, the drawing rate typically will be in the range of about 3.0 to about 30.0 feet per minute, preferably about 7.0 to about 20.0 feet per minute, and most preferably about 7.0 to about 15.0 feet per minute.

In utilizing the method of this invention to prepare hollow fiber membranes, the precipitation solution used for the outer quench bath preferably is different from that used for the center quench fluid, although the two can be the same. It probably will be preferred to utilize different solutions in order to more precisely control the phase inversion rate so that a symmetric (isotropic) membrane is produced. In hollow fiber production, the center quench and outer quench are different phenomena. At center quench, a small volume of solution is used, which is almost in a static mode as compared with the casting solution.

Conversely, the outer quench bath is present in large volumes and in a dynamic mode. By controlling the solvent content of the two quench solutions, the phase inversion rate is controlled so as to produce an isotropic membrane. Solvent diffusion out of the casting solution will occur at a different rate at the inner and outer surfaces if the same precipitation solution is used. By adjusting the solvent and swelling agent content of the two solutions, the precipitation (or phase inversion) rate will be equilibrated, resulting in an isotropic membrane.

The presence of the catalyst in the center quench solution enables the preparation of a hollow fiber membrane having a protein non-adsorptive inner surface. It is possible to have the catalyst in either the center or outer solution or both.

The precise spinning conditions are adjusted in order to yield hollow fibers meeting the desired physical requirements of inner diameter and wall thickness. Centering of the central aperture of the spinnerette is required in order to achieve a fiber having a uniform wall thickness. Any spinnerette suitable for the preparation of hollow fiber membranes may be used to prepare the membranes of this invention. The spinning conditions left to be adjusted are the flow rate and pressure of the casting solution, and the flow rate and pressure of the center quench fluid. These adjustments are well within the knowledge and ability of one of ordinary skill in this art. The preferred temperature for the casting solution will be in the range of ambient temperatures, although higher temperatures, e.g., up to about 70° C., may be employed to reduce the viscosity of the casting solution.

The dimensional and porosity characteristics of the membranes of this invention will depend on the desired end use as well as the various factors discussed above with respect to membrane preparation. Generally speaking, membranes can be prepared which possess a pore diameter of between about 0.01 microns and several microns. The inner diameter of the hollow fibers can range from about 100 to several thousand microns. The wall thickness can range from about ten to several hundred microns.

Following the quench bath, the hollow fiber is washed in water to remove residual solvents, non-solvents and swelling agents. Standard hollow fiber water wash procedures are used. It may be desired to treat the hollow fiber membranes with a humectant, such as glycerine, or a surfactant to improve membrane wettability. For example, the fibers may be soaked overnight in a 10-30% (vol/vol) glycerine bath. This step is optional. The fibers are then dried and prepared for use. The fibers may, for example, be bundled and potted in a cartridge.

In the preferred embodiment of this invention, isotropic hollow fiber membranes are prepared according to the process diagrammed in FIG. 1. This process was used in preparing the membranes of Example I. Casting solution 12, which is maintained under nitrogen atmosphere, is drawn through conduit 16 by means of pump 44 to spinnerette 18, first passing through filter 42 to eliminate undissolved particles. Casting solution 12 is fed through a ring-shaped orifice in exit port 26 of spinnerette 18 to form the hollow fiber membrane.

Simultaneously, center quench solution 10, which also is maintained under nitrogen atmosphere, is drawn through conduit 14 by means of pump 40 to spinnerette 18, first passing through filter 38 to eliminate undissolved particles. Center quench solution 10 is fed through a second orifice at the center of the ring-shaped orifice in exit port 26 of spinnerette 18 to maintain the hollow center of the membrane.

For purposes of this invention, the fiber is spun directly into the precipitation medium. Spinnerette exit port 26 is located below surface 22 of outer quench bath 20 such that casting solution 12 and center quench 10 emerge from exit port 26 directly into outer quench bath 20. Precipitation begins immediately and hollow fiber membrane 28 is formed. Membrane 28 is drawn through outer quench bath 20 via rollers 30. Membrane 28 is then guided from outer quench bath 20 to pickup roll 32, which is partially submerged in wash bath 34. Water spray 36 is directed to the top of pickup roll 32 for further washing of membrane 28. Following the water bath, membrane 28 is dried and may be treated with a humectant or surfactant as described above. Membrane 28 is then dried and prepared for use.

The protein non-adsorptive polysulfone-based hollow fiber membranes of this invention will find utility in industrial or pharmaceutical filtration and fractionation processes. These membranes exhibit good tensile strength, high flux, low fouling properties and very low protein adsorption. Membranes can be prepared which exhibit high rejection of high molecular weight species and low rejection of lower molecular weight species.

The membranes of this invention are excellently suited for many biotechnology applications including plasmapheresis. The membranes are equally well suited for immobilization of enzymes or other reactive agents due to their high surface area and high flux. The fibers can thus be used in immobilization reactors, diagnostic kits, etc. The membranes of this invention may also be used for cell culture, either for fermentation reactions or in artificial organs, or the like.

Preparation of Flat Sheet Membranes

Either supported or non-supported isotropic flat sheet membranes can be made by the method of this invention. That is, the flat membranes can be prepared either with or without an integral supporting material. If an integral support is used, it preferably will be a nonwoven polyester or polypropylene material, although other supports may be used. Non-supported, or self-supported, flat sheet membranes can be fabricated by casting the casting solution directly onto a nonporous surface such as glass, stainless steel, or the like.

For either type, the casting solution is cast onto a rigid nonporous support, such as glass or stainless steel. Where supported membranes are prepared, the nonporous support is covered with a reinforcement material (e.g., nonwoven polyester) which will become an integral support. Since the membrane is supported during precipitation, precipitation can be at a slower rate than the hollow fiber membranes described above. This affords greater flexibility in preparing the casting and precipitation solutions. However, the guidelines given above will apply generally to flat sheet membrane formation as well.

Membrane casting may be with a casting knife, and membranes may be cast onto the support at the desired thickness (i.e., 2.0 to 15.0 mils, preferably 4.0 to 10.0 mils). The membrane is cast onto the support directly in the precipitation bath, without exposure to air. When membrane formation is complete, the membrane separates from the nonporous support. However, if reinforcement material is used, it becomes an integral part of the membrane.

The membrane is water washed to remove residual solvents, non-solvents, and swelling agents. Standard water wash procedures are used. It may be desired to treat the membrane with glycerine or a surfactant to improve membrane wettability. For example, the membrane optionally may be soaked in a 10-30% (vol/vol) glycerin bath. The membrane is then dried and prepared for use.

The examples which follow are given for illustrative purposes and are not meant to limit the invention described herein. The following abbreviations have been used throughout in describing the invention:

DMF—dimethylformamide
ft—foot (feet)
Hg—mercury
hr—hour(s)
ID—inner diameter
IgG—immunoglobulin G
IPA—isopropyl alcohol
L—liter(S)
$m^2$—square meters
min—minute
ml—milliliter(s)
mm—millimeter
NMP—N-methylpyrrolidone
PS—polysulfone
psi—pounds per square inch
%—percent
THF—tetrahydrofuran
$\mu$m—micrometer(s)
vol—volume
wt—weight

EXAMPLE 1

Preparation of 0.2 Micron Fibers

Hollow fiber membranes having 0.2 micron mean pore sizes were prepared with and without a catalyst in the center coagulation solution. These membranes demonstrate the claimed invention in a variety of embodiments. The casting solution and outer coagulation solution was the same for all membranes as follows:

| Casting Solution | |
|---|---|
| Udell ™ 3500 Polysulfone | 11.6 wt % |
| BIOPOL ™ XP-5 Prepolymer | 11.0 wt % |
| Cyclododecanone | 7.7 wt % |
| NMP | 69.7 wt % |
| Outer Precipitation Solution | |
| Isopropanol | 20 vol % |
| Water | 20 vol % |
| NMP | 60 vol % |

The center precipitation solution was the same as the outer precipitation solution with the exception of addition of a catalyst in the membranes of the invention. The catalyst plus NMP concentration was maintained at 60 vol. %.

Table I indicates the amount and type of catalyst added for each membrane and shows the performance of each membrane.

The spinning procedures followed the wet spinning process described above. The overall process is depicted in FIG. 1. A tube-in-tube spinnerette was made by inserting a glass capillary tube into a heavy wall precision bore glass tube and positioned concentrically with a short glass sleeve which also served to separate the casting solution and center quench solution. The diameters of the glass capillary and precision bore glass tube were selected on the basis of the inside diameter required for the hollow fiber. For example, a typical spinnerette used to prepare membrane had the following dimensions:

| Precision Bore Glass Tube ID: | 1,500 μm |
|---|---|
| Glass Capillary OD: | 1,100 μm |
| Glass Capillary ID: | 900 μm |
| Glass Capillary Recess: | 400 μm |

Prior to casting solution delivery, the center quench solution was flowed through the spinnerette while the spinnerette was elevated above the precipitation tank to keep the glass capillary open by an uninterrupted positive pressure. When the casting solution was extruded through the spinnerette, the spinnerette was lowered into the precipitation (outer quench) bath immediately. The casting solution left the spinnerette in a downward direction and the fiber was brought through two 90° turns by guiding rollers to an upward direction. The fiber was then carried out of the precipitation tank to the take-up roll. The take-up roll was partially submerged in a water bath with a water spray on the top of the roll.

When a sufficient amount of fiber was collected on the take-up roll, the fiber bundle was removed and was cut into lengths and both ends tied with yarn. The bundles were put into a water bath overnight for further water washing. After water washing, the bundles were soaked overnight in a 10-30% (vol/vol) glycerine bath. Finally, the bundles were dried in a 60° C. oven for 20 minutes. The fibers were potted into cartridges and tested for pure water permeation rate [PWP], protein permeation rate [PR], and protein sieving coefficient (SC). The measurements were made with respect to 3 g/l of gamma-globulin solution after 30 minutes operated at a transmembrane pressure of 1-2 psi. The burst pressure of the membranes was higher than 65 psi.

TABLE I

| Fiber | Catalyst | | Performance | | |
|---|---|---|---|---|---|
| (Lot No.) | Type | wt. % | [PWP] (gfd/psi) | [PR] (gfd/psi) | [SC] (%) |
| MF-78 | — | 0 | 182 | 8 | 72 |
| MF-95 | NaHCO₃ | 0.08 | 320 | 38 | 97 |
| MF-58 | NaNO₃ | 0.08 | 307 | 29 | 99 |
| MF-70 | Na₂B₄O₇.10H₂O | 0.1 | 248 | 28 | 97 |

EXAMPLE 2

Preparation of 0.45 Micron Fibers

Hollow fiber membranes having 0.45 micron mean pore sizes were prepared with and without catalysts as described in Example 1. The casting solution and outer coagulation solution were as follows:

| Casting Solution | |
|---|---|
| Udell ™ 3500 Polysulfone | 10.0 wt % |
| BIOPOL ™ XP-5 Prepolymer | 10.5 wt % |
| Cyclododecanone | 10.0 wt % |
| NMP | 69.5 wt % |
| Outer Coagulation Solution | |
| Ethanol | 20.0 vol % |
| Water | 20.0 vol % |
| NMP | 60.0 vol % |

The center precipitation solution was the same as the outer precipitation solution with the exception of addition of a catalyst in the membrane of the invention. The catalyst plus NMP concentration was maintained at 60 wt. %. Table II indicates the performance of membranes with and without catalyst.

TABLE II

| Fiber | Catalyst | | Performance | | |
|---|---|---|---|---|---|
| (Lot No.) | Type | Wt % | [PWP] (gfd/psi) | [PR] (gfd/psi) | (SC) (%) |
| MF-205 | — | 0 | 142 | 13 | 89 |
| MF-182 | NaHCO₃ | 0.08 | 450 | 60 | >99 |

I claim:

1. A process for forming a substantially protein non-adsorptive microporous polysulfone hollow fiber membrane, comprising:
   (a) preparing, in a solvent for polysulfone, a casting solution comprising about 8.0 to about 35.0 wt. % of a polysulfone polymer, about 1.0 to about 20.0 wt. % of a hydrophilic isocyanate end-capped polyurethane prepolymer, and a pore-forming component,
   (b) preparing an outer precipitation solution comprising a solvent for polysulfone, a nonsolvent for polysulfone, and a swelling agent,
   (c) preparing a center precipitation solution comprising a solvent for polysulfone, a nonsolvent for polysulfone, a swelling agent, and a polymerization catalyst in an amount effective to prevent prepolymer from completely leaching out of said membrane,
   (d) providing a precipitation bath containing said outer precipitation solution and having a hollow fiber-forming spinnerette partially immersed therein,
   (e) extruding said casting solution and said center precipitation solution through said spinnerette directly into said precipitation bath to form an extruded hollow fiber membrane
   (f) drawing said extruded hollow fiber membrane through said precipitation bath, and
   (g) drying said extruded hollow fiber membrane.

2. The process of claim 1 wherein the hydrophilic isocyanate end-capped polyurethane prepolymer is a polyol made up of at least 75% oxyethylene monomers, said polyol having a molecular weight of about 7,000 to about 30,000, said polyol having essentially all of the hydroxyl groups capped with aliphatic or cycloaliphatic polyisocyanates.

3. The process of claim 1 in which said extruded hollow fiber membrane is drawn through said precipitation bath at a rate between about 3.0 and about 30.0 feet per minute.

4. The process of claim 1 in which said casting solution comprises about 9.0 to about 18.0 wt. % polysulfone.

5. The process of claim 1 wherein said polymerization catalyst is a water-soluble salt consisting of a monovalent cation of the alkali metal family or a divalent cation of the alkaline-earth metal family and an anion.

6. The process of claim 5 wherein said anion is selected from carbonate, bicarbonate, borate, phosphate, nitrate, silicate, aluminate, and hydroxide.

7. The process of claim 6 in which said polymerization catalyst is sodium bicarbonate, sodium nitrate or sodium borate.

8. The process of claim 1 in which the outer precipitation solution of step (b) further comprises a polymerization catalyst.

9. The process of claim 1 in which said solvent for polysulfone is N-methyl-pyrrolidone, dimethylformamide, N-N-dimethylacetamide, chloroform or 4-butyrolactone.

10. The process of claim 1 in which said pore-forming component is selected from alkanols, polyols, polyglycols or cycloketones.

11. The process of claim 10 in which said pore-forming component is methanol, t-butanol, acetone, cyclododecanone, 4-hydroxybutyric acid or polyethylene glycol.

12. The process of claim 1 in which said nonsolvent for polysulfone comprises water, methanol, ethanol, propanol, butanol, ethylene glycol, acetone or methyl ethyl ketone.

13. The process of claim 1 in which said swelling agent comprises isopropyl alcohol, ethanol, triethylene glycol, nitrobenzene, tetrahydrofuran, dioxane, dimethyl carbonate, dimethyl sulfone, diethyl phosphate or dimethyl sulfoxide.

14. The process of claim 1 in which said outer precipitation solution comprises about 10.0 to 70.0 wt. % solvent, about 10.0 to 80.0 wt. % swelling agent and about 5.0 to 40.0 wt. % non-solvent.

15. The process of claim 1 in which said center precipitation solution comprises about 10.0 to 70.0 wt. % solvent, about 10.0 to 80.0 wt. % swelling agent, about 5.0 to 40.0 wt. % non-solvent, and about 0.01 to 1.0 wt. % polymerization catalyst.

16. The process of claim 1 in which said precipitation solutions comprise N-methyl-pyrrolidone, water and isopropyl alcohol.

17. A microporous polysulfone hollow fiber membrane made by the process of claim 1.

* * * * *